United States Patent
Ozaki et al.

(10) Patent No.: US 7,803,895 B2
(45) Date of Patent: Sep. 28, 2010

(54) ORGANOSILICON POLYMER AND METHOD OF MANUFACTURING THEREOF

(75) Inventors: Masaru Ozaki, Chiba (JP); Shinya Oguri, Chiba (JP); Yasue Mizutani, Chiba (JP)

(73) Assignee: Dow Corning Toray Company, Ltd., Tokyo (JP)

( * ) Notice: Subject to any disclaimer, the term of this patent is extended or adjusted under 35 U.S.C. 154(b) by 163 days.

(21) Appl. No.: 12/092,371

(22) PCT Filed: Nov. 2, 2006

(86) PCT No.: PCT/JP2006/322425

§ 371 (c)(1),
(2), (4) Date: May 1, 2008

(87) PCT Pub. No.: WO2007/052845

PCT Pub. Date: May 10, 2007

(65) Prior Publication Data

US 2009/0124782 A1 May 14, 2009

(30) Foreign Application Priority Data

Nov. 4, 2005 (JP) ............................ 2005-320259

(51) Int. Cl.
*C08G 77/04* (2006.01)
(52) U.S. Cl. .................... 528/26; 528/22; 528/31
(58) Field of Classification Search .................. 528/26
See application file for complete search history.

(56) References Cited

FOREIGN PATENT DOCUMENTS

| | | | |
|---|---|---|---|
| DE | 10214139 A1 | 5/2003 | |
| EP | 0640658 A2 | 3/1995 | |
| JP | 01217040 A | 8/1989 | |
| JP | 07060008 A | 3/1995 | |
| JP | 07082379 A | 3/1995 | |
| JP | 2002179535 A | * | 6/2002 |
| JP | 2004/124083 A | 4/2004 | |
| WO | WO 2006/001458 A2 | 1/2006 | |
| WO | WO 2006/040964 A1 | 4/2006 | |
| WO | WO 2006/070903 A1 | 7/2006 | |
| WO | WO 2006/135036 A1 | 12/2006 | |
| WO | WO 2007/026727 A1 | 3/2007 | |

OTHER PUBLICATIONS

English language abstract for DE 10214139 extracted from espacenet.com, dated Dec. 19, 2008.
English language abstract for JP 01217040 extracted from PAJ database, dated Dec. 19, 2008, 5 pages.
English language translation and abstract for JP 07060008 extracted from PAJ database, dated Dec. 19, 2008, 37 pages.
English language translation and abstract for JP 07082379 extracted from PAJ database, dated Dec. 19, 2008, 44 pages.
English language translation and abstract for JP 2004-124083 extracted from PAJ database, dated Dec. 19, 2008, 67 pages.
PCT International Search Report for PCT/JP2005/011864, dated Jan. 20, 2006, 5 pages.
PCT International Search Report for PCT/JP2005/018405, dated Mar. 22, 2006, 6 pages.
PCT International Search Report for PCT/JP2005/024196, dated Mar. 20, 2006, 3 pages.
PCT International Search Report for PCT/JP2006/312088, dated Sep. 22, 2006, 3 page.
PCT International Search Report for PCT/JP2006/317033, dated Nov. 27, 2006, 3 pages.
PCT International Search Report for PCT/JP2006/322425, dated Feb. 20, 2007, 3 pages.

* cited by examiner

*Primary Examiner*—Randy Gulakowski
*Assistant Examiner*—Lindsay Nelson
(74) *Attorney, Agent, or Firm*—Howard & Howard Attorneys PLLC

(57) ABSTRACT

A novel organosilicon polymer, the main chain of which is composed of siloxane units and silalkylene units and to which are bonded organic groups with amide bonds linked to silicon atoms of the molecule.

3 Claims, No Drawings

ORGANOSILICON POLYMER AND METHOD OF MANUFACTURING THEREOF

RELATED APPLICATIONS

This application claims priority to and all the advantages of International Patent Application No. PCT/JP2006/322425, filed on Nov. 2, 2006, which claims priority to Japanese Patent Application No. JP 2005-320259, filed on Nov. 4, 2005.

TECHNICAL FIELD

The present invention relates to a novel organosilicon polymer, the main chain of which is composed of siloxane units and silalkylene units and to which are bonded organic groups with amide bonds linked to silicon atoms of the molecule. The present invention also relates to a method of manufacturing the aforementioned organosilicon polymer.

BACKGROUND ART

Japanese Unexamined Patent Application Publication (hereinafter referred to as "Kokai") H01-217040, Kokai H07-60008, Kokai H07-82379 and Kokai 2004-124083 disclose an organosilicone polymer, the main chain of which is composed of siloxane units and silalkylene units. Kokai H01-217040 discloses the use of the organosilicon polymer for organic resin as a modifier. Kokai H07-60008 discloses the use of the organosilicon polymer for an alkali-proof antifoaming agent, since the organosilicon polymer has better alkali-proof properties than an organopolysiloxane that consists only of siloxane units. Kokai 2004-124083 discloses the use of the organosilicon polymer for a cosmetic material in the form of an aqueous emulsion.

For a method of manufacturing the organosilicon polymer, Kokai H01-217040 discloses a method wherein an addition polymerization in the presence of hydrosilylation catalyst is carried out between a diorganopolysiloxane, which contains hydrogen atoms bonded to silicon atoms only on both molecular terminals, and an alkadiene, which is capped at both molecular terminals with vinyl groups. Kokai H07-60008 discloses a method wherein an addition polymerization in the presence of a hydrosilylation catalyst is carried out between a diorganopolysiloxane that has alkenyl groups bonded to silicon atoms only on both molecular terminals and a diorganopolysiloxane that contains hydrogen atoms bonded to silicon atoms only on both molecular terminals.

However, the aforementioned organosilicon polymers are limited with regard to their properties and fields of application. This is because the silicon-bonded organic groups thereof are limited only to the following optionally substituted organic groups: methyl, ethyl, or similar alkyl groups; cyclopentyl, cyclohexyl, or similar cycloalkyl groups; phenyl, tolyl, or similar aryl groups; benzyl, phenethyl, or similar aralkyl groups; 3-chloropropyl, 3,3,3-trifluoropropyl, or similar halogenated alkyl groups.

It is an object of the invention to provide a novel organosilicon polymer, the main chain of which is composed of siloxane units and silalkylene units and to which are bonded organic groups with amide bonds linked to silicon atoms of the molecule. It is another object of the invention to provide an efficient method of manufacturing the aforementioned organosilicon polymer.

DISCLOSURE OF INVENTION

The invention provides an organosilicon polymer, the main chain of which is composed of siloxane units and silalkylene units and to which are bonded organic groups with amide bonds linked to silicon atoms of the molecule, said groups being represented by the following general formula:

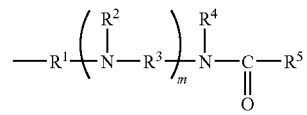

{where $R^1$ is a bivalent hydrocarbon group; $R^2$ is a hydrogen atom, a univalent hydrocarbon group, or a group represented by the following general formula:

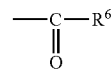

(where $R^6$ is a hydrogen atom, a univalent hydrocarbon group, a univalent hydrocarbon group that contains a hydroxyl group, a univalent hydrocarbon group that contains a carboxyl group, or a univalent hydrocarbon group with ether bonds); $R^3$ is a bivalent hydrocarbon group; $R^4$ is a hydrogen atom or a univalent hydrocarbon group; $R^5$ is a hydrogen atom, univalent hydrocarbon group, a univalent hydrocarbon that contains a hydroxyl group, a univalent hydrocarbon group that contains a carboxyl group, or a univalent hydrocarbon group with ether bonds; and "m" is an integer from 0 to 5}.

The method of the invention for manufacturing the aforementioned organosilicon polymer consists of subjecting a diorganopolysiloxane (A), which contains alkenyl groups bonded to silicon atoms only on both molecular terminals and to which are bonded organic groups with amide bonds linked to silicon atoms of the molecule, said groups being represented by the following general formula:

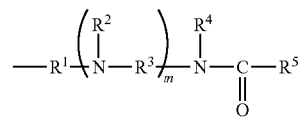

{where $R^1$ is a bivalent hydrocarbon group; $R^2$ is a hydrogen atom, a univalent hydrocarbon group, or a group represented by the following general formula:

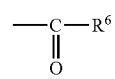

(where $R^6$ is a hydrogen atom, a univalent hydrocarbon group, a univalent hydrocarbon group that contains a hydroxyl group, a univalent hydrocarbon group that contains a carboxyl group, or a univalent hydrocarbon group with ether bonds); $R^3$ is a bivalent hydrocarbon group; $R^4$ is a hydrogen atom or a univalent hydrocarbon group; $R^5$ is a hydrogen atom, univalent hydrocarbon group, a univalent hydrocarbon that contains a hydroxyl group, a univalent hydrocarbon group that contains a carboxyl group, or a univalent hydrocarbon group with ether bonds; and "m" is an integer from 0 to 5}; and a diorganopolysiloxane (B) having hydrogen atoms bonded to silicon atoms only on both molecular terminals to addition polymerization in the presence of a hydrosilylation catalyst (C).

EFFECTS OF INVENTION

The organosilicon polymer of the present invention is a novel compound, the main chain of which is composed of siloxane units and silalkylene units and to which are bonded organic groups with amide bonds linked to silicon atoms in the molecule. The method of the invention makes it possible to efficiently produce the aforementioned novel organosilicon polymer.

DETAILED DESCRIPTION OF THE INVENTION

Let us first consider in detail the organosilicon polymer of the invention.

The organosilicon polymer of the invention is a novel compound, the main chain of which is composed of siloxane units and silalkylene units and to which are bonded organic groups with amide bonds linked to silicon atoms of the molecule, said groups being represented by the following general formula:

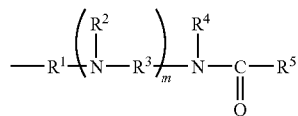

In the above formula, $R^1$ represents a bivalent hydrocarbon group, such as a methylene, ethylene, propylene, butylene, pentylene, hexylene, decylene, or a similar alkylene group; a phenylene, tolylene, xylylene, or a similar arylene group, preferably a bivalent hydrocarbon group with 1 to 10 carbon atoms, more preferably, an alkylene group, and most preferably, a propylene group.

In the above formula, $R^2$ is a hydrogen atom, a univalent hydrocarbon group, or a group represented by the following general formula:

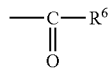

A univalent hydrocarbon group designated by $R^2$ may be exemplified by a methyl, ethyl, propyl, butyl, pentyl, hexyl, heptyl, octyl, nonyl, decyl, dodecyl, tridecyl, pentadecyl, heptadecyl, or a similar chain alkyl group; a cyclopentyl, cyclohexyl, or a similar cycloalkyl group; a propenyl, butenyl, hexenyl, heptenyl, decenyl, dodecenyl, heptadecenyl, hexadecenyl, or a similar alkenyl group that does not have carbon-carbon double bonds on molecular terminals; a phenyl, tolyl, xylyl, or a similar aryl group; a benzyl, phenethyl, or a similar aralkyl group. Preferably, this should be a univalent hydrocarbon group with 1 to 20 carbon atoms, especially a chain alkyl group. In the above formula, $R^6$ is a hydrogen atom, a univalent hydrocarbon group, a univalent hydrocarbon group that contains a hydroxyl group, a univalent hydrocarbon group that contains a carboxy group, or a univalent hydrocarbon group that contains ether bonds. The univalent hydrocarbon group designated by $R^6$ may be the same as those defined above for $R^2$, especially a chain alkyl group and an alkenyl group. The univalent hydrocarbon groups that are designated by $R^6$ and contain hydroxyl groups may also be exemplified by the groups of the following formulae:

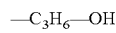

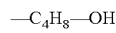

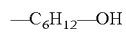

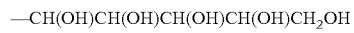

The univalent hydrocarbon groups that are designated by $R^6$ and contain carboxyl groups may also be represented by the following formula:

where $R^7$ is a bivalent hydrocarbon group. Specific examples are the following: methylene, ethylene, propylene, butylene, pentylene, hexylene, heptylene, octylene, nonylene, decylene, dodecylene, tridecylene, tetradecylene, pentadecylene, hexadecylene, heptadecylene, octadecylene, dodecenyl ethylene, or a similar alkylene group; ethylenylene, propenylene, or a similar alkenylene; a phenylene, tolylene, xylylene, or a similar arylene group. The univalent hydrocarbon groups that are designated by $R^6$ and contain carboxyl groups can be represented by the groups of the following formulae:

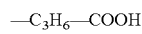

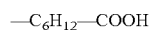

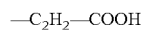

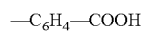

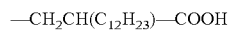

Furthermore, the univalent hydrocarbon groups that are designated by $R^6$ and contain ether bonds are represented by the following general formula:

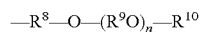

In this formula, $R^8$ is a bivalent hydrocarbon group represented by a methylene, ethylene, propylene, pentylene, or a similar alkylene group; a phenylene, tolylene, xylylene, or a similar arylene group, preferably, an alkylene group, especially, a methylene group. In the above formula, $R^9$ designates an alkylene group with 2 to 4 carbon atoms, such as an ethylene, propylene, and a butylene group, preferably, an ethylene group and a propylene group. Furthermore, in the above formula, $R^{10}$ designates a hydrogen atom, an alkyl group, or an acyl group. An alkyl group designated by $R^{10}$ may be exemplified by a methyl, ethyl, propyl, butyl, pentyl, hexyl, heptyl, octyl, nonyl, decyl, and a dodecyl group. An acyl group designated by $R^{10}$ may be represented by an acetyl group and a propionyl group. In the above formula, "n" is a number between 0 and 40. The aforementioned univalent hydrocarbon groups that are designated by $R^6$ and contain ether bonds can be represented by the groups of the following formulae:

—CH₂—O—C₂H₄O—C₁₂H₂₅

—CH₂—O—(C₂H₄O)₂—CH₃

—CH₂—O—(C₂H₄O)₄.₅—C₁₂H₂₅

—CH₂—O—(C₂H₄O)₂(C₃H₆O)₂—C₁₀H₂₁

In the above formula, R³ designates a bivalent hydrocarbon group which can be exemplified by the same groups as those designated by R¹. In the same formula, R⁴ designates a univalent hydrocarbon group which can be exemplified by the same hydrocarbon groups as those designated by R². In the same formula, R⁵ designates a hydrogen atom, a univalent hydrocarbon group, a univalent hydrocarbon group that contains a hydroxyl group, a univalent hydrocarbon group that contains a carboxyl group, or a univalent hydrocarbon group that contains ether bonds; the groups designated by R⁵ are exemplified by the group as those designated by R⁶. In the above formula, "m" is an integer from 0 to 5, preferably 0 or 1.

The above-described organosilicon polymer contains at least one of the aforementioned organic groups with amide bonds. The content of these groups should constitute 0.01 to 20 mole %, preferably 0.05 to 10 mole %, and even more preferably, 0.1 to 10 mole % of total amount of the siloxane units of the organosilicon polymer. There are no special restrictions with regard to viscosity of the organosilicon polymer, but it may be recommended to provide viscosity not exceeding 100,000 mPa·s, preferably equal to or less than 10,000 mPa·s at 25° C. As has been mentioned above, the main chain of this organosilicon polymer consists of siloxane units and silalkylene units. There are no restrictions with regard to the molecular structure of the polymer, and the main chain of the organosilicon polymer may be linear, cyclic, or branched, of which linear is preferable.

The aforementioned siloxane units are represented by the following general formula:

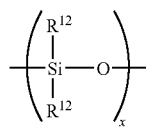

where both R¹² may be the same or different and designate organic groups with amide bonds or optionally substituted univalent hydrocarbon groups without aliphatic unsaturated bonds. The univalent hydrocarbon groups of R¹² can be exemplified by methyl, ethyl, propyl, butyl, pentyl, hexyl, heptyl, octyl, nonyl, decyl, or similar chain alkyl groups; cyclopentyl, cyclohexyl, or similar cycloalkyl groups; phenyl, tolyl, xylyl, or similar aryl groups; benzyl, phenethyl, or similar aralkyl groups; and 3-chloropropyl, 3,3,3-trifluoropropyl, or similar halogenated alkyl groups. The organic groups with amide bonds designated by R¹² are exemplified by the same groups as mentioned above. In the above formula, "x" is an integer equal to or greater than 1.

The aforementioned silalkylene units may be represented also by the following formula:

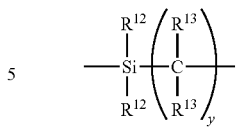

where R¹² may be the same or different and designate organic groups with amide bonds or optionally substituted univalent hydrocarbon groups without aliphatic unsaturated bonds. These groups can be exemplified by the same groups as given above. In the above formula, both R¹³ may be the same or different and designate optionally substituted univalent hydrocarbon groups that do not contain aliphatic unsaturated bonds, or hydrogen atoms. The univalent hydrocarbon groups of R¹³ may be exemplified by the same groups as those for R¹². In the above formula, "y" is an integer equal to or greater than 2.

At room temperature, the aforementioned organosilicon polymer may be liquid, gum-like, or paste-like. There are no special limitations with regard to a number-average molecular weight of the polymer but it is recommended to have it equal to or greater than 5×10⁴, preferably equal to or greater than 1×10⁵, and even more preferably, equal to or greater than 15×10⁴. It recommended that viscosity be equal to or greater than 1×10⁵ mPa·s. Alkenyl groups and silicon-bonded hydrogen atoms originated from the raw material may be present on the molecular terminals of the organosilicon polymer. The terminals groups on both molecular terminals may be the same or different. When addition polymerization is carried out with the mole number of the alkenyl groups in the below-mentioned component (A) greater than the mole number of the silicon-bonded hydrogen atoms in below-described component (B), then predominantly alkenyl groups will exist on the molecular terminals. When the addition polymerization is carried out with equivalent quantities of the aforementioned alkenyl groups and the silicon-bonded hydrogen atoms, then predominantly silicon-bonded hydrogen atoms will exist on the molecular terminals. Furthermore, when the addition polymerization is carried out with the total mole number of alkenyl groups contained in the below-described components (A) and (D) greater than the mole number of silicon-bonded hydrogen atoms in component (B), then predominantly alkenyl groups will exist on the molecular terminals. When the addition polymerization is carried out with equivalent quantities of the aforementioned groups and hydrogen atoms, then the silicon-bonded hydrogen atoms and the alkenyl groups will exist on both molecular terminals, and when the addition polymerization is carried out with the total mole number of alkenyl groups lower than the mole number of hydrogen atoms, than silicon-bonded hydrogen atoms will exist on the molecular terminals. The terminal siloxane units can be exemplified by dimethylvinylsiloxy groups, dimethylallylsiloxy groups, dimethylhexenylsiloxy groups, or similar dialkylalkenylsiloxy groups; and dimethylhydrogensiloxy group. It is possible that the dimethylhydrogensiloxy groups are hydrolyzed into dimethylhydroxysiloxy groups. When an organopolysiloxane is used which is synthesized from the above components with the use of terminal capping agents so that one of the molecular terminals is capped with a silicon-bonded hydrogen atom or a silicon-bonded alkenyl group and the other terminal with a trialkylsiloxy group, then the terminal siloxane units turn into trialkylsiloxy groups.

The following is a detailed description of a method of the invention for manufacturing the aforementioned organosilicon polymer.

The method of the invention consists of subjecting a diorganopolysiloxane (A), which contains alkenyl groups bonded to silicon atoms only on both molecular terminals and to which are bonded organic groups with amide bonds linked to silicon atoms of the molecule, said groups being represented by the following general formula:

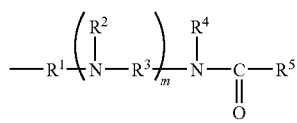

{where $R^1$ is a bivalent hydrocarbon group; $R^2$ is a hydrogen atom, a univalent hydrocarbon group, or a group represented by the following general formula:

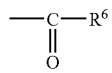

(where $R^6$ is a hydrogen atom, a univalent hydrocarbon group, a univalent hydrocarbon group that contains a hydroxyl group, a univalent hydrocarbon group that contains a carboxyl group, or a univalent hydrocarbon group with ether bonds); $R^3$ is a bivalent hydrocarbon group; $R^4$ is a hydrogen atom or a univalent hydrocarbon group; $R^5$ is a hydrogen atom, univalent hydrocarbon group, a univalent hydrocarbon that contains a hydroxyl group, a univalent hydrocarbon group that contains a carboxyl group, or a univalent hydrocarbon group with ether bonds; and "m" is an integer from 0 to 5}; and a diorganopolysiloxane (B) having hydrogen atoms bonded to silicon atoms only on both molecular terminals to addition polymerization in the presence of a hydrosilylation catalyst (C).

The alkenyl groups of component (A) may be exemplified by vinyl, allyl, butenyl, pentenyl, hexenyl, heptenyl, octenyl, nonenyl, and decenyl. The vinyl, allyl, and hexenyl groups are preferable. The meanings of $R^1$, $R^2$, $R^3$, $R^4$, $R^5$, $R^6$, and "m" in the organic groups with amide bonds contained in component (A) are the same as defined for these designations above. Other silicon-bonded groups contained in component (A) may be exemplified by methyl, ethyl, propyl, butyl, pentyl, hexyl, heptyl, octyl, nonyl, decyl, stearyl, or similar alkyl groups; cyclopentyl, cyclohexyl, or similar cycloalkyl groups; phenyl, tolyl, xylyl, or similar aryl groups; benzyl, phenethyl, or similar aralkyl groups; 3-chloropropyl, 3,3,3-trifluoropropyl, or similar halogenated alkyl groups. Most preferable are methyl and phenyl groups. There are no special restrictions with regard to viscosity of component (A). However, in order to achieve the most favorable handleability and workability, the viscosity at 25° C. should not exceed 100,000 mPa·s, and preferably should not exceed 50,000 mPa·s.

There are no special restrictions also with regard to the preparation of the organopolysiloxane of component (A). For example, this organopolysiloxane can be prepared by various methods. One method consists of causing a reaction between an organopolysiloxane having alkenyl groups bonded to silicon atoms only on molecular terminals and amino groups bonded to silicon atoms of the molecule and carboxylic acid, hydroxycarboxylic acid, carboxylic acid with ether bonds, or another carboxylic acid. Another method consists of causing a reaction between an organopolysiloxane having alkenyl groups bonded to silicon atoms only on molecular terminals and amino groups bonded to silicon atoms of the molecule and acid chloride of carboxylic acid, hydroxycarboxylic acid, carboxylic acid with ether bonds, or another carboxylic acid.

Another method consists of causing a reaction between organopolysiloxane having alkenyl groups bonded to silicon atoms only on molecular terminals and amino groups bonded to silicon atoms of the molecule and acid anhydride of carboxylic acid, hydroxycarboxylic acid, carboxylic acid with ether bonds, or another carboxylic acid. Still another method consists of causing a reaction between an organopolysiloxane having alkenyl groups bonded to silicon atoms only on molecular terminals and amino groups bonded to silicon atoms of the molecule and butylolactone or a similar intramolecular ester compound.

The diorganopolysiloxane of component (B) is the one that has hydrogen atoms bonded to silicon atoms only on both molecular terminals. Other groups that can be bonded to silicon atoms may be exemplified by methyl, ethyl, propyl, butyl, pentyl, hexyl, heptyl, octyl, nonyl, decyl, or similar alkyl groups; a cyclopentyl, cyclohexyl, or similar cycloalkyl groups; phenyl, tolyl, xylyl, or similar aryl groups; benzyl, phenethyl, or similar aralkyl groups; 3-chloropropyl, 3,3,3-trifluoropropyl, or similar halogenated alkyl groups. Most preferable are methyl and phenyl groups. Component (B) has essentially a linear molecular structure but within the limits that do not cause gelling, the obtained organosilicone polymer may have a partially branched molecular structure.

There are no special restrictions with regard to viscosity of component (B). However, in order to achieve the most favorable handleability and workability, the viscosity at 25° C. should not exceed 100,000 mPa·s, and preferably should not exceed 1,000 mPa·s. The aforementioned diorganopolysiloxane of component (B) may be exemplified by a dimethylpolysiloxane having both molecular terminals capped with dimethylhydrogensiloxy groups or by such a dimethylpolysiloxane wherein some of the methyl groups are substituted with ethyl groups, phenyl groups, 3,3,3-trifluoropropyl groups, or the like.

The manufacturing method of the invention is characterized by subjecting aforementioned components (A) and (B) to an addition-polymerization reaction. However, the method may also include addition polymerization of a diorganosiloxane (D), which contains alkenyl groups bonded to silicon atoms only on both molecular terminals. Alkenyl groups of component (D) are the same as alkenyl groups of component (A), of which vinyl, allyl, and hexenyl groups are most preferable. Silicon-bonded groups other than alkenyl groups may be exemplified by groups other than organic groups of component (A) that have amide bonds, of which methyl and phenyl groups are preferable. Component (D) has an essentially linear molecular structure, but within the limits that do not cause gelling, the obtained organosilicon polymer may have a partially branched molecular structure. There are no special restrictions with regard to viscosity of component (D). However, in order to achieve the most favorable handleability and workability, the viscosity at 25° C. should not exceed 100,000 mPa·s, and preferably should not exceed 50,000 mPa·s.

The aforementioned diorganopolysiloxane of component (D) may be exemplified by a dimethylpolysiloxane having both molecular terminals capped with dimethylvinylsiloxy groups; a diorganopolysiloxane wherein a part of the methyl groups contained in the dimethylpolysiloxane is substituted with ethyl groups, phenyl groups, 3,3,3-trifluoropropyl groups, or the like; and a diorganopolysiloxane wherein vinyl groups contained in the dimethylpolysiloxane or the diorganopolysiloxane are substituted with allyl groups, hexenyl groups, or the like.

The method of the invention is carried out by subjecting aforementioned components (A) and (B), or components (A), (B), and (D) to addition polymerization, or by further adding a diorganopolysiloxane that has hydrogen atoms or alkenyl groups bonded to silicon atoms only on one of the molecular terminals. Such a diorganopolysiloxane may be used for adjusting molecular weight of the obtained organosilicon polymer. Furthermore, in case of addition polymerization, addition of the organopolysiloxane having silicon-bonded hydrogen atoms or alkenyl groups to side molecular chains may lead to the formation of branches in the molecular structure. This component should be added in an amount needed for cross-linking the obtained organosilicon polymer and also for not making it insoluble in organic solvents. The alkenyl groups that can be used in the aforementioned alkenyl-containing diorganosiloxanes may be represented by vinyl, allyl, butenyl, pentenyl, hexenyl, heptenyl, octenyl, nonenyl, and decenyl groups, of which vinyl and allyl groups are most preferable. Silicon-bonded groups other than the silicon-bonded hydrogen atoms and alkenyl groups contained in the aforementioned diorganopolysiloxanes may be represented by methyl, ethyl, propyl, butyl, pentyl, hexyl, heptyl, octyl, nonyl, decyl, or similar alkyl groups; cyclopentyl, cyclohexyl, or a similar cycloalkyl groups; phenyl, tolyl, xylyl, or similar aryl groups; benzyl, phenethyl, or similar aralkyl groups; 3-chloropropyl, 3,3,3-trifluoropropyl, or similar halogenated alkyl groups. Most preferable are methyl and phenyl groups. The aforementioned diorganopolysiloxanes have an essentially linear molecular structure, but may also have a partially branched structure as well. There are no special restrictions with regard to viscosity of these diorganopolysiloxanes. It is recommended, however, to have their viscosity equal to or less than 100,000 mPa·s, and preferably equal to or less than 5,000 mPa·s at 25° C.

Specific examples of the aforementioned diorganopolysiloxanes are the following: a copolymer of a methylhydrogensiloxane and a dimethylsiloxane capped at both molecular terminals with trimethylsiloxy groups; a copolymer of a methylhydrogensiloxane and a dimethylsiloxane capped at both molecular terminals with dimethylhydrogensiloxy groups; a diorganopolysiloxane wherein a part of methyl groups contained in the copolymer of a methylhydrogensiloxane and a dimethylsiloxane is substituted with ethyl groups, phenyl groups, 3,3,3-trifluoropropyl groups, or the like; a copolymer of a methylvinylsiloxane and a dimethylsiloxane having both molecular terminals capped with trimethylsiloxy groups; a copolymer of a methylvinylsiloxane and a dimethylsiloxane capped at both molecular terminals with dimethylvinylsiloxy groups; a diorganopolysiloxane wherein a part of methyl groups contained in the copolymer of a methylvinylsiloxane and a dimethylsiloxane is substituted with ethyl groups, phenyl groups, 3,3,3-trifluoropropyl groups, or the like; a dimethylpolysiloxane having one molecular terminal capped with dimethylhydrogensiloxy groups and the other molecular terminal capped with trimethylsiloxy groups; a dimethylpolysiloxane having one molecular terminal capped with dimethylvinylsiloxy groups and the other terminal capped with trimethylsiloxy groups; a diorganopolysiloxane wherein a part of methyl groups contained in their dimethylpolysiloxane group is substituted with ethyl groups, phenyl groups, 3,3,3-trifluoropropyl groups, or the like; and a diorganopolysiloxane wherein vinyl groups contained in their dimethylpolysiloxane are substituted with aryl groups, and hexenyl groups.

In compounding components (A) and (B) for addition polymerization by the method of the invention, the aforementioned components should be used in such quantities that the content of silicon-bonded atoms of component (B) is in the range of 0.5 to 1.5 moles per 1 mole of alkenyl groups of component (A), or about 1.0 mole if necessary to obtain an organosilicon polymer of a high molecular weight. If the addition-polymerization reaction is carried out with components (A), (B), and (D), the amount of silicon-bonded hydrogen groups of component (B) should be in the range of 0.5 to 1.5 mole per 1 mole of alkenyl groups in the sum of components (A) and (D), or about 1.0 mole if necessary to obtain an organosilicon polymer of a high molecular weight.

In the method of the invention, a hydrosilylation catalyst of component (C) accelerates the addition-polymerization reaction of components (A), (B), and (D) and is used for the preparation of an organosilicon polymer from siloxane and alkylene units. Examples of component (C) are a platinum-type catalyst, rhodium-type catalyst, and a palladium-type catalyst. The platinum-type catalyst is most preferable in view of its remarkable catalytic effect. Examples of the platinum-type catalysts are the following: finely powdered platinum, platinum on a fine silica powder as a carrier, platinum on active-carbon carrier, chloroplatinic acid, alcohol solution of a chloroplatinic acid, a platinum-alkenylsiloxane complex, a platinum-olefin complex, and a platinum-carbonyl complex. The most preferable is the platinum-alkenylsiloxane complex. Such a platinum-alkenylsiloxane complex may be exemplified by the following compounds: 1,3-divinyl-1,1,3,3-tetramethyl disiloxane, 1,3,5,7-tetramethyl-1,3,5,7-tetravinyl cyclotetrasiloxane, alkenylsiloxanes having a part of their methyl groups substituted with ethyl, phenyl, or similar groups, and alkenylsiloxanes having a part of their vinyl groups substituted with allyl, hexenyl, or similar groups. The platinum-alkenylsiloxane complex most preferable due to its stability is the 1,3-divinyl-1,1,3,3-tetramethyldisiloxane. In order to further improve stability of the aforementioned platinum-alkenylsiloxane complexes, they may be combined with 1,3-divinyl-1,1,3,3-tetramethyldisiloxane, 1,3-diallyl-1,1,3,3-tetramethyldisiloxane, 1,3-divinyl-1,3-dimethyl-1,3-diphenyldisiloxane, 1,3-divinyl-1,1,3,3-tetraphenyldisiloxane, 1,3,5,7-tetramethyl-1,3,5,7-tetravinyl cyclotetrasiloxane, or similar alkenylsiloxanes or dimethylsiloxane oligomers, or other organosiloxane oligomers. The most preferable of the above are alkenylsiloxanes.

There are no special restrictions in the method of the invention with regard to the amounts in which component (C) can be added, but in order to efficiently accelerate the addition polymerization reaction, it is recommended to add this component in such an amount that in terms of weight units the catalytic metal is contained in the catalyst in an amount of 0.1 to 1,000 ppm, preferably 0.1 to 500 ppm, and most preferably, 1 to 50 ppm per total weight of components (A) and (B). When the addition-polymerization reaction is carried out with components (A), (B), and (D), the content of the catalytic metal in the catalyst should be in the range of 0.1 to 1,000 ppm, preferably 0.1 to 500 ppm, and most preferably, 1 to 50 ppm per total weight of components (A), (B), and (D).

In the method of the invention, the addition-polymerization reaction is carried out in the presence of components (A), (B), and (C), or in the presence of components (A), (B), (D), and (C). Components (A), (B), (D), and (C) can be added in an arbitrary sequence. For example, component (C) can be added with stirring to a mixture of components (A) and (B) while this mixture is heated from room temperature to a predetermined temperature. According to another procedure, component (B) can be added with stirring to a mixture of components (A) and (C) while this mixture is heated from room temperature to a predetermined temperature. Alternatively, component (C) can be added with stirring to a mixture of components (A), (B), and (D) while this mixture is heated from room temperature to a predetermined temperature, or component (B) can be added with stirring to a mixture of components (A), (D), and (C) while this mixture is heated from room temperature to a predetermined temperature. Although the addition polymerization reaction can be carried out at room temperature, for acceleration of the process it is recommended to conduct the reaction with heating, but at a temperature not exceeding 150° C., preferably not exceeding 120° C.

According to the method of the invention, the obtained organosilicon polymer may be dispersed and diluted in non-reactive silicone oils and organic oils. The silicone oil is represented by one having a linear, partially-branched linear, cyclic, or branched molecular structure. Most preferable are silicone oils having linear and cyclic molecular structures. Specific exampled of such oils are the following: a dimethylpolysiloxane having both molecular terminals capped with trimethylsiloxy groups, a methylphenylpolysiloxane having both molecular terminals capped with trimethylsiloxy groups, a copolymer of a methylphenylsiloxane and a dimethylsiloxane having both molecular terminals capped with trimethylsiloxy groups, a copolymer of a dimethylsiloxane and a methyl (3,3,3-trifluoropropyl) siloxane having both molecular terminals capped with trimethylsiloxy groups, or a similar linear-chain silicone oil; decamethylpentacyclosiloxane, pentamethylpentaphenylpentacyclosiloxane, or a similar cyclic silicone oil.

The organic oils can be exemplified by isobutene, isopentane, neopentane, methylpentane, dimethylbutane, methylhexane, ethylpentane, dimethylpentane, trimethylbutane, methylheptane, dimethylhexane, trimethylpentane, methyloctane, methylnonane, or a similar isoparaffin; n-butane, n-pentane, n-hexane, n-heptane, n-octane, n-nonane, n-decane, n-pentadecane, n-octadecane, or a similar n-paraffin; hexyl laurate, isopropyl myristate, myristyl myristate, cetyl myristate, 2-octyldodecyl myristate, isopropyl pamitate, 2-ethylhexyl palmitate, butyl stearate, decyl oleate, 2-octyldodecyl oleate, myristyl lactate, cetyl lactate, lanolin acetate, stearic alcohol, cetostearic alcohol, oleic alcohol, avocado oil, almond oil, olive oil, cacao oil, jojoba oil, sesame oil, safflower oil, soybean oil, camellia oil, squalane oil, persic oil, castor oil, mink oil, cotton seed oil, coconut oil, yolk oil, beef tallow, lard, polypropyleneglycol mono-oil, neopentylglycol-2-ethylhexanoate, or a similar glycolester oil; triglyceride isostearate, triglyceride of a palm oil fatty acid, or a similar polyhydric alcohol ester oil; polyoxyethylenelauryl ether, and polyoxypropylenecetyl ether, or a similar polyoxyalkylene ether oil.

Most preferable is decamethylpentacyclosiloxane or a similar cyclic silicone oil, as well as dimethylpolysiloxane, or a similar linear-chain silicone oil, or the iso-paraffin type oil. There are no special restrictions with regard to viscosity of the aforementioned oils at 25° C., but it is recommended to have viscosity not exceeding $1 \times 10^5$ mPa·s, preferably not exceeding $5 \times 10^4$ mPa·s, and most preferably not exceeding $3 \times 10^4$ mPa·s. There are special restrictions with regard to the amount in which this component can be added. It may be recommended to add the oil in an amount of 0.1 to 5,000 parts by weight, preferably 1 to 1,000 parts by weight per 100 parts by weight of the obtained organosilicon polymer.

According to the method of the invention, the addition polymerization reaction between components (A) and (B) or components (A), (B), and (D) can be carried out in water. More specifically, the components (A) and (B) or components (A), (B), and (D) are emulsified in water to form an emulsion, and then the addition polymerization reaction is carried out with the addition of component (C).

Emulsification can be carried out by dispersing a mixture of the aforementioned components in water by means of a homomixer, paddle mixer, Henschel mixer, homodisper, colloidal mixer, propeller-type stirrer, homogenizer, in-line continuous-mode emulsifier, ultrasonic emulsifier, vacuum kneeder, or a similar known stirrer or mixer. According to another method, separate emulsions can be prepared by dispersing the respective diorganopolysiloxanes in water and then mixing the prepared emulsions with each other.

In order to improve stability of the emulsion obtained by emulsifying the component mixture in water, the emulsion can be combined with surface-active agents. Examples of such surface-active agents are the following: anionic surface-active agents such as hexylbenzenesulfonic acid, octylbenzenesulfonic acid, decylbenzenesulfonic acid, dodecylbenzenesulfonic acid, cetylbenzenesulfonic acid, myristylbenzenesulfonic acid, or sodium salts of the above; cationic surface-active agents such as octyltrimethyl ammonium hydroxide, dodecyltrimethyl ammonium hydroxide, hexadecyltrimethyl ammonium hydroxide, octyldimethylbenzyl ammonium hydroxide, decyldimethylbenzyl ammonium hydroxide, dioctadecyldimethyl ammonium hydroxide, beef tallow trimethyl ammonium hydroxide, coconut oil trimethyl ammonium hydroxide; and nonionic surface-active agents such as polyoxyalkylene alkyl ether, polyoxyalkylene alkyl phenol, polyoxyalkylene alkyl ester, polyoxyalkylene sorbitane ester, polyethylene glycol, polypropylene glycol, ethylene oxide adduct of diethylene glycol trimethyl nonanol, or similar polyester-type nonionic surface-active agents. Most preferable of the above are nonionic-type surface-active agents since their effect on the products of addition polymerization is low.

There are no special restrictions with regard to the amounts in which the surface-active agents can be added, but it may be recommended to add them in an amount of 0.01 to 50 parts by weight, in particular, 0.1 to 20 parts by weight, per 100 parts by weight of the sum of the aforementioned components. There are no restrictions also with regard to the amount of water, but it is preferable to add water in an amount of 10 to 200 parts by weight per 100 parts by weight of the sum of the aforementioned diorganopolysiloxanes.

In the method of the invention, component (C) can be added to the emulsion as it is, but, if necessary, it can be first emulsified in water to form a catalytic emulsion (C). Such a catalytic emulsion can be prepared by dispersing component (C) in water with the use of the known stirrers and mixers. For improving stability, this emulsion can be combined with the same surface-active agents as those mentioned above. Component (C) can be preliminarily dispersed in the surface-active agent, the mixture is then added to the emulsion of the aforementioned diorganopolysiloxanes, and the product is then dispersed in water. Surface-active agents used for this purpose may be the same as those mentioned above. Most preferable are nonionic surface-active agents that do not noticeably influence the hydrosilylation reaction. In this case, the surface-active agents should be added in an amount of 0.01 to 1,000 parts by weight per 100 parts by weight of component (C).

In accordance with the method of the invention, component (C) is added to the emulsion of a mixture of components (A) and (B), or of components (A), (B), and (D), the components are uniformly mixed, and the mixture is held in quiescence. Alternatively, for acceleration of the addition polymerization reaction, the mixture can be heated, but to a temperature not exceeding 100° C., preferably to a temperature not exceeding 70° C.

EXAMPLES

The organosilicon polymer and the manufacturing method of the invention will further be explained in more detail with reference to application examples. In these examples, all viscosities have values corresponding to 25° C.

Application Example 1

A mixture was prepared from 94.3 parts by weight of a dimethylpolysiloxane of the following average formula:

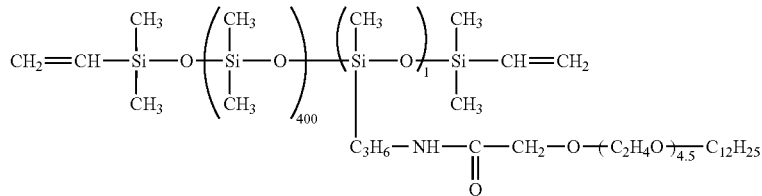

capped at both molecular terminals with dimethylvinylsiloxy groups and having a viscosity of 2600 mPa·s and 5.7 parts by weight of a dimethylpolysiloxane of the following average formula:

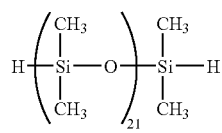

capped at both molecular terminals with dimethylhydrogensiloxy groups and having a viscosity of 18 mPa·s (where 1.14 moles of the silicon-bonded hydrogen atoms contained in the dimethylpolysiloxane correspond to 1 mole of vinyl groups contained in the dimethylpolysiloxane capped at both molecular terminals with dimethylvinylsiloxy groups). Following this, a 1,3-divinyl-1,1,3,3-tetramethyldisiloxane solution of a platinum-1,3-divinyl-1,1,3,3-tetramethyldisiloxane complex (with 4.0 wt. % concentration of metallic platinum) was added to the dimethylpolysiloxanes in an amount (in terms of weight units) of 40 ppm of the metallic platinum per total weight of the dimethylpolysiloxanes. The components were mixed. The obtained liquid mixture was heat-treated for 3 hours at 100° C. in a hot-air circulation oven. As a result, a viscous liquid having a viscosity of 430,000 mPa·s was obtained. Nuclear magnetic resonance spectral analysis (hereinafter referred to as "NMR") and infrared spectral analysis (hereinafter referred to as "IR") confirmed that the obtained product constituted the organosilicon polymer represented by the average formula given below. Furthermore, the obtained organosilicon polymer was analyzed by means of gel-permeation chromatography (hereinafter referred to as "GPC"), which showed the value of a weight-average molecular weight with reference to dimethylpolysiloxane equal to 260,000.

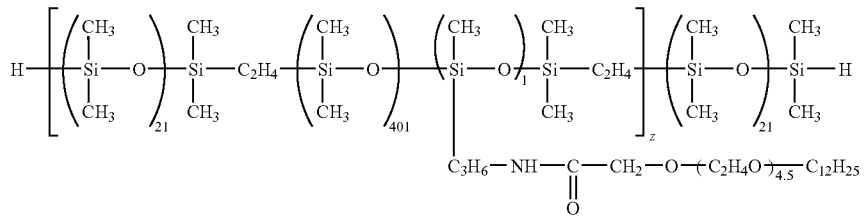

(where "z" is a number equal to or greater than 1).

Application Example 2

A mixture was prepared from 94.2 parts by weight of a dimethylpolysiloxane of the following average formula:

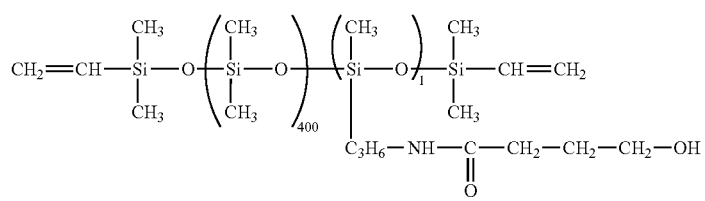

capped at both molecular terminals with dimethylvinylsiloxy groups and having a viscosity of 2400 mPa·s and 5.8 parts by weight of a dimethylpqlysiloxane of the following average formula:

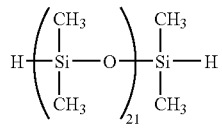

capped at both molecular terminals with dimethylhydrogensiloxy groups and having a viscosity of 18 mPa·s (where 1.14 moles of the silicon-bonded hydrogen atoms contained in the dimethylpolysiloxane correspond to 1 mole of vinyl groups contained in the dimethylpolysiloxane capped at both molecular terminals with dimethylvinylsiloxy groups). Following this, a 1,3-divinyl-1,1,3,3-tetramethyldisiloxane solution of a platinum-1,3-divinyl-1,1,3,3-tetramethyldisiloxane complex (with 4.0 wt. % concentration of metallic platinum) was added to the dimethylpolysiloxanes in an amount (in terms of weight units) of 40 ppm of the metallic platinum per total weight of the dimethylpolysiloxanes. The components were mixed. The obtained liquid mixture was heat-treated for 3 hours at 100° C. in a hot-air circulation oven. As a result, a viscous liquid having a viscosity of 230,000 mPa·s was obtained. NMR analysis and IR analysis confirmed that the obtained product constituted the organosilicon polymer represented by the average formula given below. Furthermore, the obtained organosilicon polymer was analyzed by means of GPC, which showed the value of a weight-average molecular weight with reference to dimethylpolysiloxane equal to 152,000.

capped at both molecular terminals with dimethylvinylsiloxy groups and having a viscosity of 280 mPa·s, 83.8 parts by weight of a dimethylpolysiloxane of the following average formula:

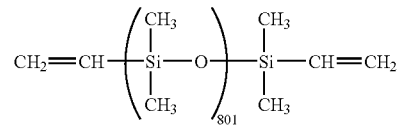

capped at both molecular terminals with dimethylvinylsiloxy groups and having a viscosity of 40,000 mPa·s, 4.7 parts by weight of dimethylpolysiloxane expressed by the following average formula:

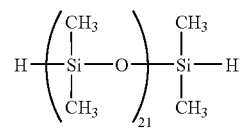

capped at both molecular terminals with dimethylhydrogensiloxy groups and having a viscosity of 18 mPa·s (where 1.04 moles of the silicon-bonded hydrogen atoms contained in the dimethylpolysiloxane correspond to 1 mole of vinyl groups contained in the dimethylpolysiloxanes of the two different types capped at both molecular terminals with dimethylvinylsiloxy groups), and 100 parts by weight of decamethylpentacyclosiloxane were poured in metered quantities into a separable flask equipped with a condenser, nitrogen supply tube, and a stirrer, and the components were mixed. The liquid

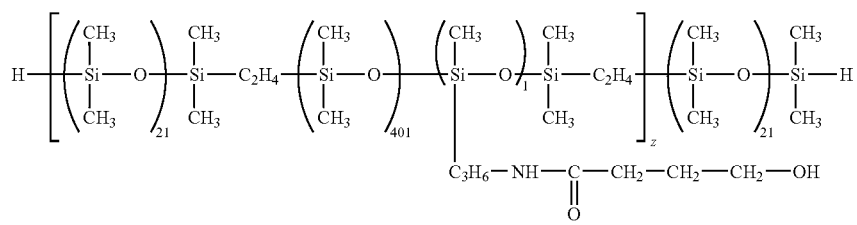

(where "z" is a number equal to or greater than 1).

Application Example 3

A mixture was prepared from 11.5 parts by weight of a dimethylpolysiloxane of the following average formula:

mixture was heated to 80° C. and following this, a 1,3-divinyl-1,1,3,3-tetramethyldisiloxane solution of a platinum-1,3-divinyl-1,1,3,3-tetramethyldisiloxane complex (with 4.0 wt. % concentration of metallic platinum) was added to the dimethylpolysiloxanes in an amount (in terms of weight units) of 12 ppm of the metallic platinum. Following this, the obtained

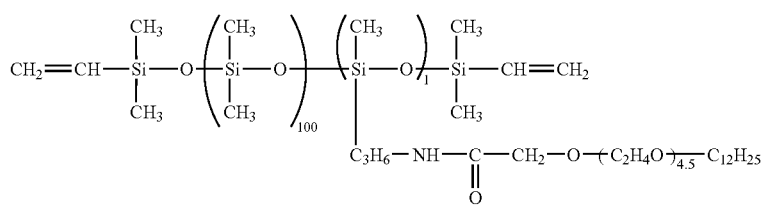

liquid mixture was heated for 3 hours at 95° C., and an addition polymerization reaction was carried out. The obtained product comprised an extremely viscous liquid mixture having a viscosity of 960,000 mPa·s. A portion of the obtained liquid mixture was heat-treated for 3 hours at 70° C. in a hot-air circulation oven. The decamethypentacyclosiloxane was removed. As a result, a gum-like substance having a viscosity higher than 6,000,000 mPa·s was obtained. NMR analysis and IR analysis confirmed that the obtained product constituted the organosilicon polymer represented by the average formula given below. Furthermore, the obtained organosilicon polymer was analyzed by means of GPC, which showed the value of a weight-average molecular weight with reference to dimethylpolysiloxane equal to 879,000.

capped at both molecular terminals with dimethylvinylsiloxy having a viscosity of 40,000 mPa·s, 5.0 parts by weight of dimethylpolysiloxane expressed by the following average formula:

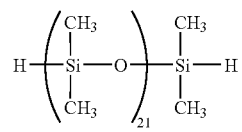

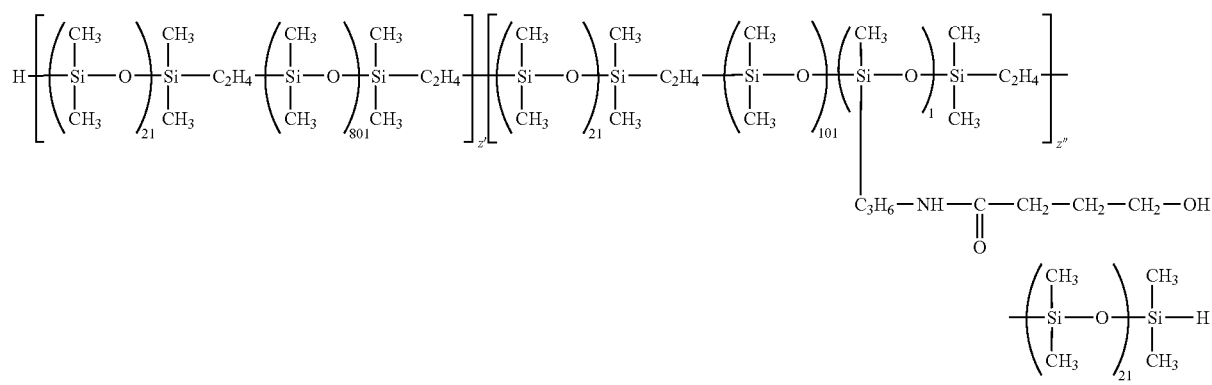

(where "z'" and "z''" are numbers equal to or greater than 1).

Application Example 4

A mixture was prepared from 11.2 parts by weight of a dimethylpolysiloxane of the following average formula:

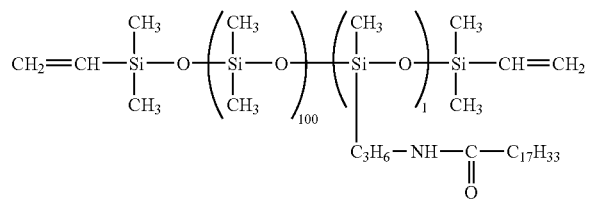

capped at both molecular terminals with dimethylvinylsiloxy groups and having a viscosity of 240 mPa·s, 83.8 parts by weight of a dimethylpolysiloxane of the following average formula:

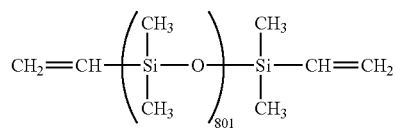

capped at both molecular terminals with dimethylhydrogensiloxy groups and having a viscosity of 18 mPa·s (where 1.10 moles of the silicon-bonded hydrogen atoms contained in the dimethylpolysiloxanes correspond to 1 mole of the total vinyl groups contained in the dimethylpolysiloxanes of the two different types capped at both molecular terminals with dimethylvinylsiloxy groups), and 400 parts by weight of decamethylpentacyclosiloxane were poured in metered quantities into a separable flask equipped with a condenser, nitrogen supply tube, and a stirrer, and the components were mixed. The liquid mixture was heated to 80° C. and following this, a 1,3-divinyl-1,1,3,3-tetramethyldisiloxane solution of a platinum-1,3-divinyl-1,1,3,3-tetramethyldisiloxane complex (with 4.0 wt. % concentration of metallic platinum) was added to the dimethylpolysiloxanes in an amount (in terms of weight units) of 12 ppm of the metallic platinum. Following this, the obtained liquid mixture was heated for 3 hours at 95° C. The obtained product comprised a viscous liquid mixture having a viscosity of 3,000 mPa·s. A portion of the obtained liquid mixture was heat-treated for 5 hours at 70° C. in a hot-air circulation oven. The decamethypentacyclosiloxane was removed. As a result, a gum-like substance having a viscosity higher than 3,500,000 mPa·s was obtained. NMR analysis and IR analysis confirmed that the obtained product constituted the organosilicon polymer represented by the average formula given below. Furthermore, the obtained organosilicon polymer was analyzed by means of GPC, which showed the value of a weight-average molecular weight with reference to dimethylpolysiloxane equal to 363,000.

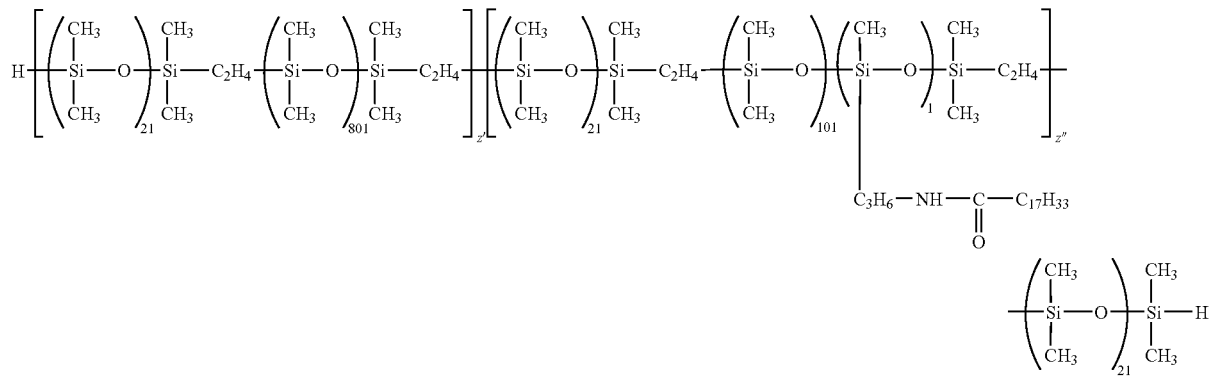

(where "z'" and "z''" are numbers equal to or greater than 1).

Application Example 5

A mixture was prepared from 6.9 parts by weight of a dimethylpolysiloxane of the following average formula:

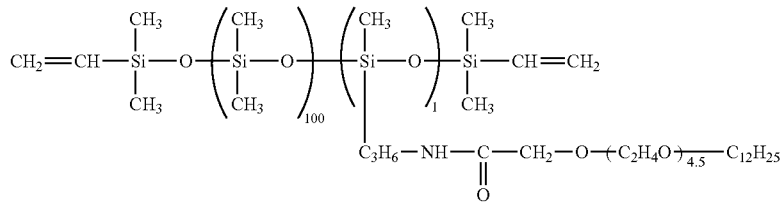

capped at both molecular terminals with dimethylvinylsiloxy groups and having a viscosity of 320 mPa·s, 50.2 parts by weight of a dimethylpolysiloxane of the following average formula:

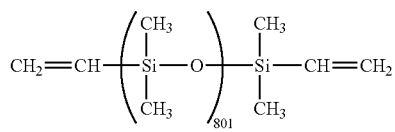

capped at both molecular terminals with dimethylvinylsiloxy having a viscosity of 40,000 mPa·s, and 2.9 parts by weight of dimethylpolysiloxane expressed by the following average formula:

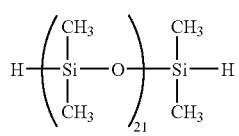

capped at both molecular terminals with dimethylhydrogensiloxy groups and having a viscosity of 18 mPa·s (where 1.07 moles of the silicon-bonded hydrogen atoms contained in the dimethylpolysiloxanes correspond to 1 mole of the total vinyl groups contained in the dimethylpolysiloxanes of the two different types capped at both molecular terminals with dimethylvinylsiloxy groups). The components were mixed and combined with 10 parts by weight of an aqueous solution that contained 16 wt. % of polyoxyethylene (4) lauryl ether (HLB=11.5) and 24 wt. % of polyoxyethylene (25) lauryl ether (HLB=19.5). After the mixture was emulsified, it was combined with 30 parts by weight of pure water and then with an isopropyl alcohol solution of a platinum 1,3-divinyl-1,1,3,3-tetramethyldisiloxane complex (with a 4.0 wt. % concentration of metallic platinum), which contained the metallic platinum (in terms of weight units) in an amount of 20 ppm per total weight of dimethylpolysiloxanes. As a result, an emulsion was prepared. This emulsion was heat-treated for 2 hours at 50° C. A portion of the obtained emulsion was combined with ethanol, and after the emulsion was destroyed and washed, and the volatile components evaporated by holding the product for one day in quiescence. As a result, a gum-like substance having a viscosity of 4,300,000 mPa·s was obtained. NMR analysis and IR analysis confirmed that the obtained product constituted the organosilicone polymer represented by the average formula given below. Furthermore, the obtained organosilicone polymer was analyzed by means of GPC, which showed the value of a weight-average molecular weight with reference to dimethylpolysiloxane equal to 423,000.

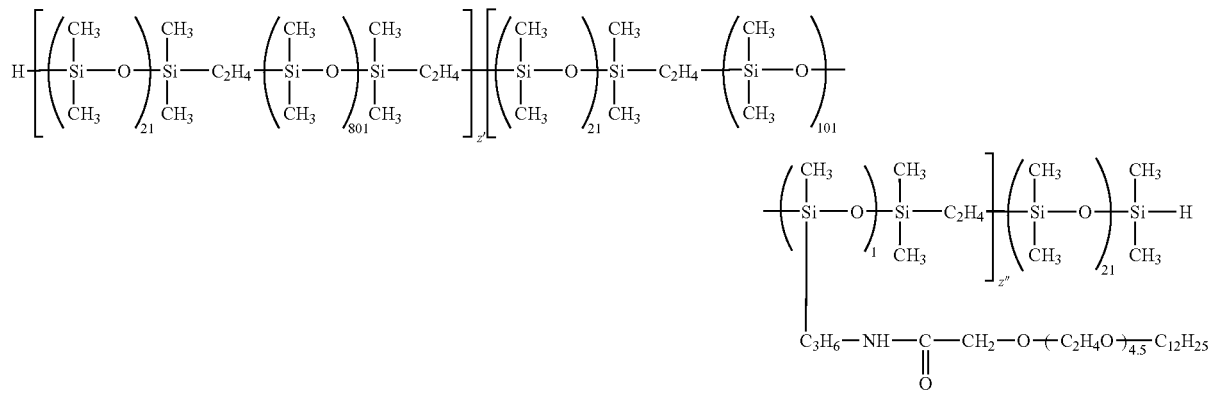

(where "z'" and "z''" are numbers equal to or greater than 1).

Application Example 6

A mixture was prepared from 8.1 parts by weight of a dimethylpolysiloxane of the following average formula:

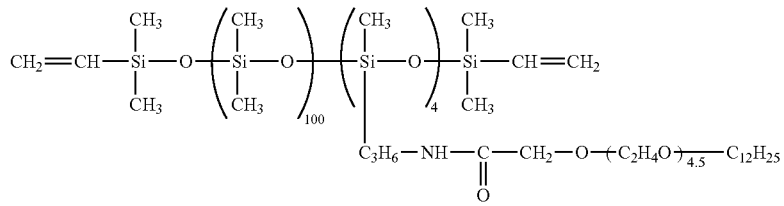

capped at both molecular terminals with dimethylvinylsiloxy groups and having a viscosity of 360 mPa·s, 49.1 parts by weight of a dimethylpolysiloxane of the following average formula:

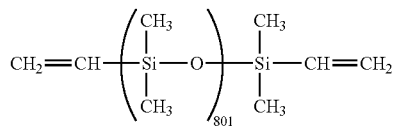

capped at both molecular terminals with dimethylvinylsiloxy having a viscosity of 40,000 mPa·s, and 2.8 parts by weight of dimethylpolysiloxane expressed by the following average formula:

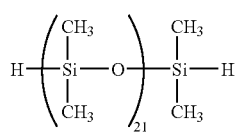

capped at both molecular terminals with dimethylhydrogensiloxy groups and having a viscosity of 18 mPa·s (where 1.06 moles of the silicon-bonded hydrogen atoms contained in the dimethylpolysiloxanes correspond to 1 mole of the total vinyl groups contained in the dimethylpolysiloxanes of the two different types capped at both molecular terminals with dimethylvinylsiloxy groups). The components were mixed and combined with 10 parts by weight of an aqueous solution that contained 16 wt. % of polyoxyethylene (4) lauryl ether (HLB=11.5) and 24 wt. % of polyoxyethylene (25) lauryl ether (HLB=19.5). After the mixture was emulsified, it was combined with 30 parts by weight of pure water and then with an isopropyl alcohol solution of a platinum 1,3-divinyl-1,1,3,3-tetramethyldisiloxane complex (with a 4.0 wt. % concentration of metallic platinum), which contained the metallic platinum (in terms of weight units) in an amount of 20 ppm per total weight of dimethylpolysiloxanes. As a result, an emulsion was prepared. This emulsion was heat-treated for 2 hours at 50° C. A portion of the obtained emulsion was combined with ethanol, and after the emulsion was destroyed and washed, and the volatile components evaporated by holding the product for one day in quiescence. As a result, a gum-like substance having a viscosity of 3,000,000 mPa·s was obtained. NMR analysis and IR analysis confirmed that the obtained product constituted the organosilicon polymer represented by the average formula given below. Furthermore, the obtained organosilicon polymer was analyzed by means of GPC, which showed the value of a weight-average molecular weight with reference to dimethylpolysiloxane equal to 396,000.

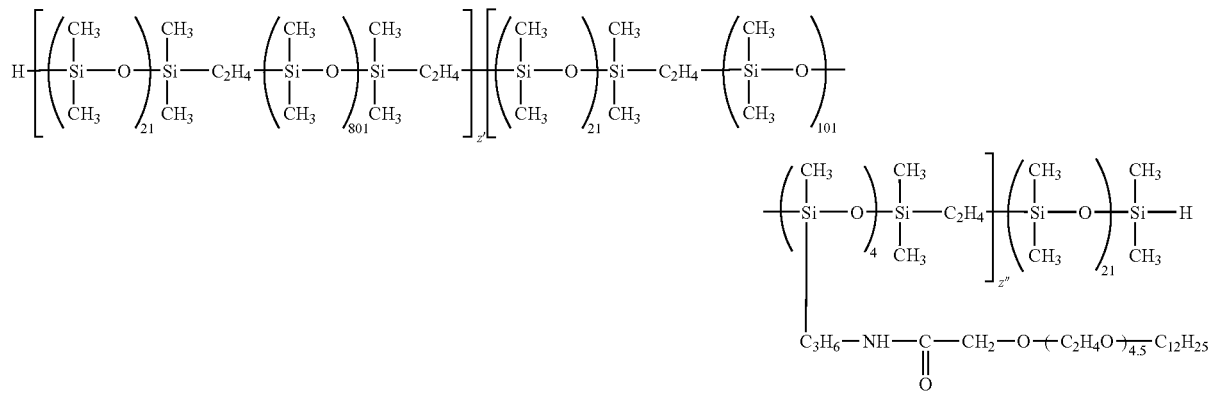

(where "z'" and "z''" are numbers equal to or greater than 1).

INDUSTRIAL APPLICABILITY

Since the organosilicon polymers of the invention demonstrate perfect characteristics of organopolysiloxanes composed only of siloxane units and excellent characteristics of amide derivatives, they may find application in the production of cosmetic materials, coating materials, additives to coating materials, mold-release agents for organic resin molding, modifiers for organic resin, lubricants, softeners, and the like, as well as for application onto substrates such as hair, skin, nails, metal, organic resin, inorganic resin, glass, ceramics, fillers, structural materials, fibers, paper, etc. In particular, the organosilicone polymers of the invention may be used as components of shampoo, hair rinse, hair make-up, hair growth substance, hair restoring substance, hair dye, or similar hair conditioning components. Furthermore, the polymers of the invention may be used as softeners for industrial fiber finishing, as detergents, and as softeners for household use, dry cleaning agents, etc.

The invention claimed is:

1. An organosilicon polymer, the main chain of which is composed of siloxane units and silalkylene units and to which are bonded organic groups with amide bonds linked to silicon atoms of the molecule, said groups being represented by the following general formula:

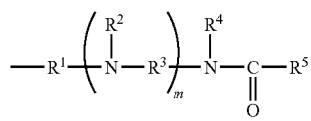

where $R^1$ is a bivalent hydrocarbon group; $R^2$ is a hydrogen atom, a univalent hydrocarbon group, or a group represented by the following general formula:

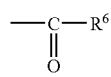

where $R^6$ is a hydrogen atom, a univalent hydrocarbon group, a univalent hydrocarbon group that contains a hydroxyl group, a univalent hydrocarbon group that contains a carboxyl group, or a univalent hydrocarbon group with ether bonds; $R^3$ is a bivalent hydrocarbon group; $R^4$ is a hydrogen atom or a univalent hydrocarbon group; $R^5$ is a hydrogen atom, univalent hydrocarbon group having 17 carbon atoms, a univalent hydrocarbon that contains a hydroxyl group, a univalent hydrocarbon group that contains a carboxyl group, or a univalent hydrocarbon group with ether bonds; and "m" is an integer from 0 to 5.

2. A method of manufacturing an organosilicon polymer, the main chain of which is composed of siloxane units and silalkylene units, by subjecting a diorganopolysiloxane (A), which contains alkenyl groups bonded to silicon atoms only on both molecular terminals and to which are bonded organic groups with amide bonds linked to silicon atoms of the molecule, said groups being represented by the following general formula:

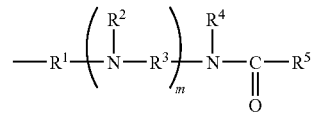

where $R^1$ is a bivalent hydrocarbon group; $R^2$ is a hydrogen atom, a univalent hydrocarbon group, or a group represented by the following general formula:

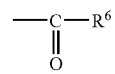

where $R^6$ is a hydrogen atom, a univalent hydrocarbon group, a univalent hydrocarbon group that contains a hydroxyl group, a univalent hydrocarbon group that contains a carboxyl group, or a univalent hydrocarbon group with ether bonds; $R^3$ is a bivalent hydrocarbon group; $R^4$ is a hydrogen atom or a univalent hydrocarbon group; $R^5$ is a hydrogen atom, univalent hydrocarbon group, a univalent hydrocarbon that contains a hydroxyl group, a univalent hydrocarbon group that contains a carboxyl group, or a univalent hydrocarbon group with ether bonds; and "m" is an integer from 0 to 5; and a diorganopolysiloxane (B) having hydrogen atoms bonded to silicon atoms only on both molecular terminals to addition polymerization in the presence of a hydrosilylation catalyst (C).

3. The method of claim 2, further comprising the step of addition polymerization of a diorganopolysiloxane (D), which contains alkenyl groups bonded to silicon atoms only on both molecular terminals and which is free of a silicon-bonded organic group with amide bonds.

* * * * *